US008546347B2

(12) United States Patent
Park et al.

(10) Patent No.: US 8,546,347 B2
(45) Date of Patent: Oct. 1, 2013

(54) COMPOSITION FOR TREATMENT AND IMPROVEMENT OF DIABETES COMPRISING CAVEOLIN AS ACTIVE INGREDIENT AND A METHOD FOR TREATMENT OF DIABETES USING IT

(75) Inventors: Sang Chul Park, Gyeonggi-do (KR); Yoon Sin Oh, Seoul (KR)

(73) Assignee: Seoul National University Industry Foundation, Seoul (KR)

( * ) Notice: Subject to any disclaimer, the term of this patent is extended or adjusted under 35 U.S.C. 154(b) by 153 days.

(21) Appl. No.: 12/736,218

(22) PCT Filed: Mar. 21, 2008

(86) PCT No.: PCT/KR2008/001609
§ 371 (c)(1),
(2), (4) Date: Oct. 20, 2010

(87) PCT Pub. No.: WO2009/116695
PCT Pub. Date: Sep. 24, 2009

(65) Prior Publication Data
US 2011/0038799 A1    Feb. 17, 2011

(51) Int. Cl.
*A01N 43/04*    (2006.01)
*A01N 63/00*    (2006.01)
*C12N 15/00*    (2006.01)
*C12N 15/63*    (2006.01)
*C07H 21/04*    (2006.01)

(52) U.S. Cl.
USPC ......... 514/44; 424/93.2; 435/320.1; 435/455; 536/23.5

(58) Field of Classification Search
USPC ............... 514/44; 424/93.2; 435/320.1, 455; 536/23.5
See application file for complete search history.

(56) References Cited

U.S. PATENT DOCUMENTS
2004/0110684 A1* 6/2004 Balligand et al. ............... 514/12

OTHER PUBLICATIONS

Barker et al., 1993, Diabetologia, 36:62-67, abstract.*
Oh et al., 2006, Journal of Cellular Biochemistry, 99: 747-758.*
Gorecki, D., 2001, Expert Opin. Emerging Drugs, 6(2): 187-198.*
Bennett, J., 2003, Gene Therapy, vol. 10, p. 977-982.*
Thomas et al., 2003, Nature Reviews/Genetics, vol. 4, p. 346-358.*
Lebedeva et al., 2003, Seminars in Cancer Biology, vol. 12, p. 169-178.*
Kodama et al., 2006, Current Medicinal Chemistry, vol. 13, p. 2155-2161.*
Sanlioglu et al., 2012, Expert Reviews in Molecular Medicine, vol. 14, e18, p. 1-14.*
Ting et al., 2006, Current Gene Therapy, vol. 6, No. 2, p. 193-214.*
Hamman et al., 2005, Biodrugs, vol. 19, No. 3, p. 165-177.*
Torchilin et al., 2003, DDT, vol. 8, No. 6, p. 259-266.*
Cohen, A.W. et al., "Caveolin-1-deficient mice show insulin resistance and defective insulin receptor protein expression in adipose tissue", Am. J. Physiol. Cell Physiol., vol. 285, (2003), pp. C222-C235.
Yamamoto, M. et al, "Caveolin Is an Activator of Insulin Receptor Signaling", The Journalof Biological Chemistry, vol. 273, No. 41, (1998), pp. 26962-26968.
Nystrom, F.H. et al., "Caveolin-1 Interacts with the Insulin Receptor and Can Differentially Modulate Insulin Signaling in Transfected Cos-7 Cells and Rat Adipose Cells", Molicular Endocrinololgy, vol. 13, (1999), pp. 2013-2024.

* cited by examiner

*Primary Examiner* — Shin-Lin Chen
(74) *Attorney, Agent, or Firm* — Nixon Vanderhye P.C.

(57) ABSTRACT

The present invention relates to a composition for the treatment and improvement of diabetes comprising caveolin as an active ingredient and a method for treating diabetes using the same, more precisely a composition comprising caveolin-1 as an active ingredient for the treatment and improvement of type II diabetes which is age-dependent but not showing obesity symptom and a method for treating diabetes using the same. The treatment method and composition of the present invention is very effective in improving and treating diabetes by regulating insulin sensitivity by increasing caveolin level in muscle tissues of type II diabetes patient which is age-dependent but not showing obesity symptom.

2 Claims, 8 Drawing Sheets

SEQUENCE LISTING

```
<160> NUMBER OF SEQ ID NOS: 6

<210> SEQ ID NO 1
<211> LENGTH: 22
<212> TYPE: DNA
<213> ORGANISM: Artificial Sequence
<220> FEATURE:
<223> OTHER INFORMATION: myogenin-sense

<400> SEQUENCE: 1
agcggctgcc taaagtggag at                                              22

<210> SEQ ID NO 2
<211> LENGTH: 24
<212> TYPE: DNA
<213> ORGANISM: Artificial Sequence
<220> FEATURE:
<223> OTHER INFORMATION: myogenin-antisense

<400> SEQUENCE: 2
ggacgtaagg gagtgcagat tgtg                                            24
```

```
<210> SEQ ID NO 3
<211> LENGTH: 22
<212> TYPE: DNA
<213> ORGANISM: Artificial Sequence
<220> FEATURE:
<223> OTHER INFORMATION: leptin-sense

<400> SEQUENCE: 3
cctgtggctt tggtcctatc tg                                              22

<210> SEQ ID NO 4
<211> LENGTH: 21
<212> TYPE: DNA
<213> ORGANISM: Artificial Sequence
<220> FEATURE:
<223> OTHER INFORMATION: leptin-antisense

<400> SEQUENCE: 4
aggcaagctg gtgaggatct g                                               21

<210> SEQ ID NO 5
<211> LENGTH: 67
<212> TYPE: DNA
<213> ORGANISM: Artificial Sequence
<220> FEATURE:
<223> OTHER INFORMATION: shlenti-cav-1

<400> SEQUENCE: 5
cggaattcca tctacaagcc caacaacttc ggttgttggg cttgtagatg tttttgatat     60
ctagaca                                                               67

<210> SEQ ID NO 6
<211> LENGTH: 21
<212> TYPE: DNA
<213> ORGANISM: Artificial Sequence
<220> FEATURE:
<223> OTHER INFORMATION: shlenti-GFP

<400> SEQUENCE: 6
aatcgcatag cgtatgccgt t                                               21
```

COMPOSITION FOR TREATMENT AND IMPROVEMENT OF DIABETES COMPRISING CAVEOLIN AS ACTIVE INGREDIENT AND A METHOD FOR TREATMENT OF DIABETES USING IT

TECHNICAL FIELD

The present invention relates to a composition for the treatment and improvement of diabetes comprising caveolin as an active ingredient and a method for treating diabetes using the same. More precisely, the present invention relates to a use of caveolin 1 as a regulator of insulin sensitivity in age-dependent type II diabetes characterized by not showing the symptoms of obesity.

BACKGROUND ART

Diabetes is classified into type I diabetes and Type II diabetes according to its dependence on insulin. Insulin dependent type I diabetes, which is dominant among diabetes, is developed by destruction of beta cells of pancreas that produce insulin, indicating that insulin is not generated in vivo. In the case of insulin resistant type II diabetes, insulin generation in pancreas is normal but insulin is not functioning in peripheral organs, which causes the disease (1).

Insulin resistance in muscle which is the main tissue to eliminate glucose and fatty acid indicates that type II diabetes is beginning. Type II diabetes is aging-dependent disease. thus, the incidence rate of type II diabetes increases as aging progresses (2). In general, type II diabetes, taking 70-80% of entire diabetes, exhibits the symptom of obesity as it progresses. However, in Asia, particularly in Korea, only 20-30% of type II diabetes patients are obese and most of the patients are not obese (3).

In the meantime, it has not been explained yet what kind of role the aging plays in type II diabetes which is age-dependent but does not exhibit the symptom of obesity. It might be one reason that a proper diabetes model has not been established. For diabetes study, animal models such as rats have been used for clinical tests, precisely ob/ob mice or OLETF rats characterized by having diabetes with the symptom of obesity when they are young are the examples (4, 5). Recently, US patent No. 2007/012487 describes the animal model for human type II diabetes produced by mating a C57BL/6 mouse and a DBA/2 mouse, which is expected to contribute greatly to studies on the treatment and improvement of type II diabetes.

Caveolaeis the intracellular invagination of 50-100 nm in size which contains 21-24 kDa structural protein called caveolin (6). Caveolin is largely divided into three groups: caveolin-1, caveolin-2 and caveolin-3. Caveolin-1 and caveolin-2 are commonly expressed in many kinds of cells and form hetero oligomer in cell membrane. In the meantime, caveolin-3 is expressed specifically in skeletal muscles and regulates muscle fiber generation (8). It has been recently reported that caveolin-1 plays an important role in regulating glucose homeostasis in adipocytes (9, 10). It has also been reported by the present inventors that caveolin-1 plays an important role in senescent phenotype (11, 12) and caveolin-1 is expressed more in aged rat tissues than in young rat tissues (13). According to the previous reports, caveolin-1 is expressed in muscle tissue (14-16), and binds to caveolin-3 specifically in muscle tissue (17). The present inventors investigated functional importance of caveolin-1 and caveolin-3 in muscle tissues. As a result, the present inventors found out that it was not caveolin-3 but caveolin-1 that played an important role in glucose absorption in differentiated muscle cells (18).

Many of patent descriptions and papers are cited in this description and presented by brackets. The cited patent descriptions and papers are attached herein as references and help clear understanding of arts and context of this patent.

DISCLOSURE

Technical Problem

During continued experiments to develop a method for treating and improving insulin resistance using offspring of a C57BL/6 mouse and a DBA mouse (referred as JYD mouse hereinafter) showing the symptoms of type II diabetes, the present inventors discovered that caveolin expression was remarkably down-regulated in muscle tissues of the animal model, compared with that in a wild-type animal. Therefore, the present inventors completed this invention by confirming that caveolin played an important role in the development and progress of type II diabetes which is age-dependent butdoes not exhibit the symptom of obesity.

Technical Solution

It is an object of the present invention to provide a composition for the treatment and improvement of diabetes comprising caveolin as an active ingredient.

It is another object of the present invention to provide a method for the treatment of diabetes using caveolin.

It is also an object of the present invention to provide a method for the prevention and treatment of diabetes related disease.

The objects and advantages of the present invention are more clearly explained in the following examples, claims and figures.

Advantageous Effects

The present inventors confirmed that caveolin-1 down-regulation in muscle tissues of a JYD mouse, the animal model for type II diabetes which is age-dependent but does not exhibit the symptom of obesity, resulted in the development of diabetes symptoms and at the same time caveolin-1 could regulate insulin sensitivity of the JYD mouse. Thus, the present inventors developed a method for treating and improving diabetes effectively by regulating insulin sensitivity by increasing caveolin level in muscle tissues in age-dependent but not obese type II diabetes patients.

DESCRIPTION OF DRAWINGS

The above and other objects, features and advantages of the present invention will become apparent from the following description of preferred embodiments given in conjunction with the accompanying drawings, in which.

MODE FOR INVENTION

Figure 1:
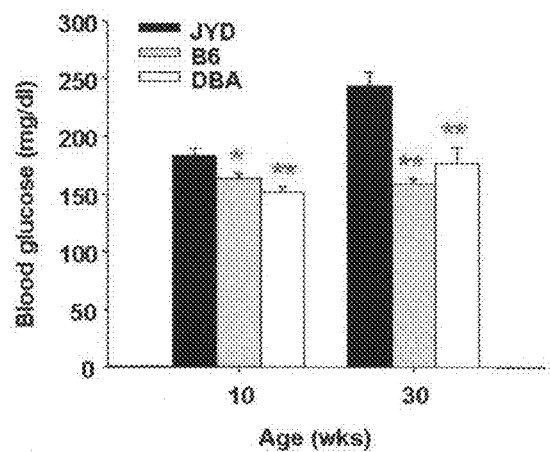
FIG. 1 is a set of graphs illustrating the blood glucose concentration, diabetes incidence rate, and weight of male JYD mice. A: mean value of blood glucose concentration with normal diet, B: incidence rate of diabetes, and C: weights of the mouse at 10 weeks and at 30 weeks. At this time, male C57BL/6 (B6) and DBA/2 (DBA) were used as the control. The value was presented as mean±standard deviation. n=45/group. *: $P<0.05$ (compared with JYD mouse), and **: $P<0.01$ (compared with JYD mouse).
Figure 1:
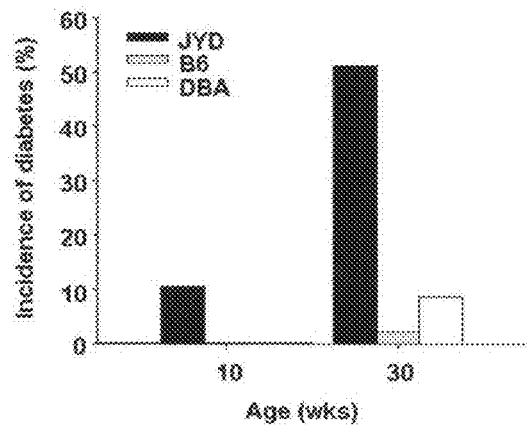
Figure 1:
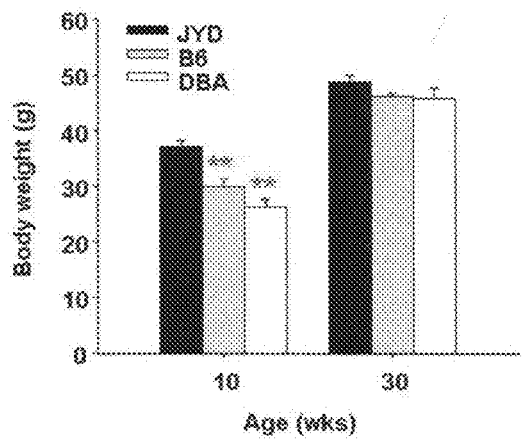

The present invention relates to a composition for the treatment and improvement of diabetes comprising caveolin as an active ingredient.

The present invention provides a composition for the treatment and improvement of diabetes which is age-dependent but does not show obesity symptom in JYD, the type II diabetes animal model.

The present invention is described in more detail in the following preferred embodiments. In this invention, 1) glucose resistance test and 2) insulin resistance test were performed in the type II diabetes mouse model JYD, and 3) glucose absorption was measured by positron emission tomography. The measured values were recorded as the control for type II diabetes predisposition. 4) Caveolin expression levels in skeletal musclesof JYD mouse and the control mouse were measured by immunodetection. Then, the composition of the present invention comprising caveolin as an active ingredient was treated to the mice. Glucose resistance, insulin resistance, glucose absorption and caveolin expression level were measured to examine progress of diabetes treatment.

According to the preferred embodiment of the present invention, caveolin is caveolin-1, caveolin-2 or caveolin-3, and more preferably caveolin-1. The composition comprising caveolin as an active ingredient herein can contain the active ingredient in the form of protein, DNA or RNA, and more preferably in the form of gene. When the composition contains the active ingredient in the form of gene, the gene is included with a vector.

When caveolin is included in the form of gene, the expression vector for eukaryotic cells to carry the caveolin gene safely into animal cells and to express caveolin therein preferably contains a promoter of a virus requiring animals as a host and a polyadenylation signal. It is also possible that caveolin can be carried by RNA virus vector or adenovirus vector, and more preferably it is delivered by short hair-pin RNA lentivirus vector or adenovirus vector. Caveolin can be administered by the insertion of the expression vector containing caveolin gene into an animal cell by the insertion of the expressed protein into an animal cell. The insertion of the expression vector containing caveolin gene into an animal cell is performed by microinjection (Capecchi, M. R., *Cell*, 22:479 (1980)), calcium phosphate co-precipitation (Graham, F. L. et al., *Virology*, 52:456 (1973)), electroporation (Neumann, E. et al., *EMBO J.*, 1:841 (1982)) or liposome mediated method (Wong, T. K. et al., *Gene*, 10:87 (1980)), but not always limited thereto.

According to the preferred embodiment of the present invention, 1) when caveolin was delivered by short hair-pin RNA virus vector, caveolin gene was first inserted into short hair-pin RNA lentivirus vector (shlenti-cav-1). Then, shRNA was produced from U6 promoter, by which GFP protein was expressed from IRES system. To investigate transfection efficiency, L6 cells were infected with lentivirus, and GFP expression in the transfected cells was measured by fluorescent microscope and protein immunodetection. The constructed RNA virus vector-caveolin was introduced in muscle of JYD mouse having diabetes. Then in vivo transfection efficiency was investigated. 2) When caveolin was delivered by adenovirus vector, infectious recombinant adenovirus was first produced by AdEasy method. Then, caveolin expressing recombinant adenovirus was inserted into shuttle plasmid. Homologous rearrangement was made in *E. coli* BJ5183 harboring this shuttle vector. Recombinant virus was selected by using kanamycin, followed by digestion using restriction enzyme. HEK293 cells were infected with the linearized recombinant adenovirus plasmid to produce the adenovirus. The adenovirus was amplified by the conventional virus amplification method, followed by separation. JYD mouse having diabetes was infected with the amplified virus via muscle, followed by immunohistochemical staining to investigate in vivo transfection efficiency.

The target subject of the composition of the present invention for the treatment and improvement of diabetes is any mammal and preferably human.

Diabetes in this invention is preferably selected from the group consisting of type I diabetes, type II diabetes, maturity onset diabetes developed in youngsters, latent autoimmune diabetes and pancreatic diabetes, and more preferably type II diabetes, and most preferably type II diabetes which is age dependent but does not show obesity, but not always limited thereto.

The composition of the present invention can include buffer containing proper amount of salt and PH regulator in order to maintain the maximum physiological activity of the active ingredient. In order for the active ingredient of the present invention to be more effective, the composition can additionally include a small amount of an enzyme. A dispersing agent or a stabilizer can also be additionally included.

The present invention relates to a method for the treatment and improvement of diabetes using the composition containing caveolin as an active ingredient.

The method for the treatment and improvement of diabetes of the present invention demonstrates excellent diabetes treatment and improvement effect by administering the composition containing caveolin as an active ingredient to a subject with diabetes, and the details are same as mentioned above regarding the composition for the treatment and improvement of diabetes.

The treatment target of diabetes herein is every mammals having diabetes and preferably human. Caveolin herein can be administered in the form of protein or any type of gene such as DNA encoding the protein and RNA, and preferably in the form of gene and more preferably in the form of DNA.

According to the preferred embodiment of the present invention, caveolin is caveolin-1, caveolin-2 or caveolin-3, and preferably caveolin-1. When the active ingredient is administered in the form of protein, it can be administered as a capsule to protect the active ingredient from being decomposed by protease. The active ingredient can also be administered in the form of pre-protein. When the active ingredient is administered in the form of gene, it can be administered with a gene vector.

According to the preferred embodiment of the present invention, caveolin can be delivered by RNA virus vector or adenovirus vector, preferably by short hair-pin RNA lentivirus vector or adenovirus vector, which would increase treatment and improvement effect by expressing DNA or protein in vivo.

Diabetes in this invention is preferably selected from the group consisting of type I diabetes, type II diabetes, maturity onset diabetes developed in youngsters, latent autoimmune diabetes and pancreatic diabetes, and more preferably type II diabetes, and most preferably type II diabetes which is age dependent but does not show obesity, but not always limited thereto.

The composition of the present invention can include buffer containing proper amount of salt and PH regulator in order to maintain the maximum physiological activity of the active ingredient. In order for the active ingredient of the present invention to be more effective, the composition can additionally include a small amount of an enzyme. A dispersing agent or a stabilizer can also be additionally included.

When the composition of the present invention contains a protein, the composition additionally contains a pharmaceutically acceptable vector, which is selected from the group consisting of carbohydrate (ex: lactose, amylose, dextrose, sucrose, sorbitol, mannitol, starch, cellulose, etc), gum acacia, calcium phosphate, alginate, gelatin, calcium silcate, microcrystalline cellulose, polyvinyl pyrrolidone, cellulose, water, syrup, salt solution, alcohol, gum arabic, vegetable oil (ex: corn oil, cotton seed oil, soybean oil, olive oil, coconut oil, etc), polyethylene glycol, methyl cellulose, methylhydroxy benzoate, propylhydroxy benzoate, talc, magnesium stearate and mineral oil, but not always limited thereto. The composition of the present invention can additionally include lubricant, wetting agent, sweetening agent, flavor, emulsifying agent, suspending agent and preservative, but not always limited thereto.

The composition of the present invention can be administered by any administration pathway designed for a pharmaceutically acceptable composition. Particularly, the composition can be administered percutaneously, orally or parenterally. The parenteral administration includes intravenous injection, hypodermic injection and intramuscular injection and intramuscular injection is more preferred.

The effective dosage of the composition of the present invention can de adjusted according to administration method, formulation method, administration pathway, age, weight, gender, health condition, diet, administration frequency, excretion and sensitivity, which is generally determined and prescribed by an experienced doctor.

The composition of the present invention can be formulated by the method that can be performed by those in the art by using a pharmaceutically acceptable vector and/or excipient in the form of unit dose or in multi-dose container. The formulation can be in the form of solution suspension or emulsion in oil or water-soluble medium, extract, powder, granule, tablet or capsule. At this time, a dispersing agent or a stabilizer can be additionally included. To maintain the maximum physiological activity of the active ingredient, a buffer containing proper amount of salt and pH regulator can be added.

The present invention relates to a method for the prevention and treatment of diabetes related disease.

The method for the prevention and treatment of diabetes of the present invention is not only effective in treating and improving diabetes but also effective in preventing and treating diabetes related disease, and details are same as mentioned above regarding the method for the treatment and improvement of diabetes.

The method for the prevention and treatment of diabetes related disease of the present invention contains the step of administering the composition comprising caveolin as an active ingredient to a subject, and the diabetes related disease herein is exemplified by hyperglycemia, hyperinsulinemia, impaired glucose resistance, impaired fasting glucose, dyslipidemia, hypertriglyceridemia and insulin resistance, etc. The target herein is every mammals having diabetes related disease and preferably human.

The present invention relates to a method for diagnosing type II diabetes in mammals containing the step of measuring the level of caveolin.

The present inventors confirmed that caveolin level was significantly lower in the muscle tissues of a mammal having diabetes than in a wild-type mammal without diabetes. Based on this result, type II diabetes could be diagnosed by measuring caveolin level. For example, diabetes can be diagnosed by quantifying caveolin mRNA and protein in the muscle tissues of a mammal and comparing the results with mRNA and protein of the control without diabetes.

The caveolin level herein indicates the level of caveolin DNA, RNA or protein, and preferably the level of caveolin RNA or protein and more preferably the level of caveolin mRNA or protein and most preferably the level of protein. The level of RNA can be measured by any conventional method, but Northern blotting and immunohistochemical staining are preferred. The level of protein can be measured by any conventional method based on antigen-antibody binding reaction, but ELISA (enzyme-linked immunosorbent assay), RIA (radioimmunoassay), sandwich assay, Western blotting on SDS-polyacrylamide gel, immuno-blotting and immunohistochemical staining are preferred, and ELISA (enzyme-linked immunosorbent assay), Western blotting on SDS-polyacrylamide gel, immuno-blotting and immunohistochemical staining are more preferred. The level of caveolin can be analyzed by quantitative method. In that case, PAGE and blotting are first performed and then colored band, band or area on photograph or film is measured by densitometer to quantify the differences.

In the method for diagnosing diabetes of the present invention, the caveolin level indicates caveolin-1 level, precisely caveolin level measured from the cells or tissues isolated from muscle tissues of a mammal. In a preferred embodiment of the present invention, when the quantified caveolin or caveolin protein is at least 20%, preferably at least 50%, more preferably at least 80% lower than that of the wild type control without diabetes, diabetes is diagnosed.

In another preferred embodiment of the present invention, the invention provides a kit for diagnosing type II diabetes in mammals containing the step of measuring caveolin level.

The diagnostic kit of the present invention is designed based on the diagnostic method of diabetes containing the step of measuring caveolin level, so it includes every details of the diagnostic method of diabetes. Therefore, the diagnostic kit of the present invention includes the step of measuring caveolin-1 level in muscle tissues of a mammal. More preferably, the caveolin-1 level measured in muscle tissues of a mammal having diabetes is compared with that of the wild-type control without diabetes.

That is, the diagnostic kit of the present invention contains an antibody against caveolin-1, a secondary antibody conjugate binding to a marker developing color when reacted with a substrate, a substrate solution for color development to react with the marker, a washing buffer, and anenzyme reaction stop solution. The diagnostic kit of the invention can additionally contain the control caveolin-1 antigen or caveolin-1 protein isolated from muscle tissues of a wild-type mammal without diabetes for the comparison with the control.

The kit can be used for the conventional protein quantification method such as ELISA (enzyme-linked immunosorbent assay), RIA (radioimmunoassay), sandwich assay, Western blotting on SDS-polyacrylamide gel, immuno-blotting, and immunohistochemical staining. The caveolin-1 level measured by the above method is compared with that of the control to diagnose type II diabetes.

Practical and presently preferred embodiments of the present invention are illustrative as shown in the following Examples.

However, it will be appreciated that those skilled in the art, on consideration of this disclosure, may make modifications and improvements within the spirit and scope of the present invention.

EXAMPLES

1. Generation of Type II Diabetes Model Mouse which is Age-dependent and does not Show Obesity Symptom C57BL/6 and DBA2 mice were purchased from Charles River Laboratory (Wilmington, Mass.), and ob/ob mice were purchased from Jackson Laboratory (Bar Harbor, Me.). To generate type II diabetes mouse model which is age-dependent but dose not show obesity, female C57BL/6 mice and male DBA/2 mice were mated to obtain the first generation (F1) mice according to the method described in US Patent Publication No. US 2007/012487. And the obtained mice were named JYD.

JYD mice had normal diet and were raised under 12 hourday/night lightcycle, except when modification was needed for a special experiment. Weight and blood glucose level were measured at 10 and 30 weeks of age. The mice showing blood glucose level of at least 250 mg/dl were diagnosed as diabetes. Age-matched C57BL/6 and DBA mice not having diabetes were used as the control. Every experiment method including treating and anesthetizing animals followed the protocol approved by Institute of Laboratory Animal Resources, College of Medicine, Seoul National University (Korea) and University of Calgary (Canada).

2. Cell Culture

L6 cells, a rat skelectal muscle cell line, were purchased from ATCC (Manassas, Va.), which was maintainedin DMEM/F12 containing with 10% FBS, 100 U/ml of penicillin and 100 μg/ml of streptomycin.

3. Glucose and Insulin Resistance Test

To test glucose resistance, the mice were fasted for 16 hours, followed by injection of glucose (2 g/kg body weight, hypodermic injection). 0, 15, 30, 60 and 120 minutes after the glucose injection, tail vein blood was taken and blood glucose level was measured using glucometer (One Touch, Lifescan, Milpitas, Calif.). To test insulin resistance, the fed mice were injected with insulin (1 U/kg body weight, hypodermic injection). 0. 15, 30, 60 and 120 minutes after the glucose injection, tail vein blood was taken and blood glucose level was measured.

4. Glucose Absorption Rate Measured by Positron Emission Tomography

Positron emission tomography was performed with dedicated small animal PET system (microPET-R4, Concorde Microsystems Inc., Knoxville, Tenn.). The mice were fasted for 18-20 hours and radioactive 18F-fluorodioxyglucose (FDG; 7.4 MBq [200 μCi] in 0.1 ml; KIRAMS, Seoul, Korea) was injected through tail vein. Whole body PET imaging was performed for 30 minutes from one hour after the 18F-FDG injection. The mice were kept anesthetized with isoflurane (0.5% in 100% oxygen) and placed on pre-heated (30° C.) pad during the experiment.

PET results were transformed to 2-dimensional ultrasonography using histogram and Fourier rebinning (FRB) and reconstructed to tomography result using expectation maximization algorithm. The reconstructed PET images were converted into % image of injected dose per gram. At this time, % ID/g indicates (count per pixel*cross calibration factor)/injected dose and 1 ml was calculated as 1 g.

5. Protein Immunodetection

DBA/2, C57BL/6, and JYD mice at 3, 10 and 30 weeks of age were sacrificed using $CO_2$ gas. Skeletal muscles (hind limb) and other tissues were excised immediately and quick-frozen in liquid nitrogen, which were stored at −70° C. To measure the phosphorylation of IRβ and Akt/PKB in vivo, the mice were fasted for 16 hours and insulin was injected (1 U/kg body weight, hypodermic injection). 30 minutes later, muscle tissues were excised quickly and stored in liquid nitrogen. The excised tissues (10-30 mg) were pulverized using liquid nitrogen, followed by lysis in 1% SDS buffer (1% SDS, mM Tris-HCl, pH 7.4, 150 mM NaCl, 1 mM EDTA, 1 mM NaF, 1 mM phenylmethylsulfonylfluoride) containing a protease inhibitor. L6 cells were lysed in lysis buffer containing 1% SDS. Protein concentration was adjusted, followed by separation on SDS-PAGE. Then, the proteins were transferred onto nitrocellulose membrane (Schleicher & Schuell Bioscence Inc., NJ), followed by reaction with the following primary antibodies anti-IRβ antibody (Upstate, Lake Placid, N.Y.), anti-IRS antibody (Upstate), anti-tubulin and anti-GLUT-4 antibody (Santa Cruz Biotechnology Inc., Santa Cruz, Calif.), anti-Akt/PKB antibody (New England BioLabs, Ipswich, Mass.), anti-PPARβ (New England BioLabs), anti-caveolin-1 antibody and anti-caveolin-3 antibody (BD Transduction, Palo Alto, Calif.), anti-phospho-IRβ antibody and anti-phospho-Akt/PKB antibody (Cell signaling technology, Berverly, Mass.) and anti-flotillin antibody (BD Transduction).

After washing the nitrocellulose membrane, the membrane was reacted with horse-radish peroxidase conjugated secondary antigen (Zymed, San Francisco, Calif.). The protein bound by immunological method was confirmed by using ECL (enhanced chemiluminescence) Western blot detection kit (Pierce, Rockford, Ill.). Each band was quantified by densitometric scanning with the exposed film.

6. Measurement of mRNA by RT-PCR

RNA was extracted from skeletal muscle and adipose tissues by using trizole solution (Sigma, St. Louis, Mo.). Reverse transcription was induced with 2 μg of the RNA. Each single stranded cDNA was amplified by PCR using myogenin and leptin specific primers (myogenin sense, 5'-AGC GGC TGC CTA AAG TGG AGA T antisense, 5'-GGA CGT AAG GGA GTG CAG ATT GTG) (leptin; sense, 5'-CCT GTG GCT TTG GTC CTA TCT G; antisense, 5'-AGG CAA GCT GGT GAG GAT CTG). PCR with myogenin cDNA was performed as follows: predenaturation at 94° C. for 5 minutes, denaturation at 94° C. for 30 seconds, annealing at 60° C. for 30 seconds, polymerization at 72° C. for 30 seconds, 30 cycles from denaturation to polymerization, and final extension at 72° C. for 5 minutes. 266 by PCR product was confirmed. PCR with leptin cDNA was performed as follows: predenaturation at 94° C. for 5 minutes, denaturation at 94° C. for 30 seconds, annealing at 61° C. for 30 seconds, polymerization at 72° C. for 30 seconds, 30 cycles from denaturation to polymerization, and final extension at 72° C. for 5 minutes. 244 by PCR product was confirmed. PCR products obtained above were electrophoresed on 1.2% agarose gel, followed by staining with EtBr (ethidium bromide) for separation.

7. Immunohistochemical Staining

<108>Skeletal muscle tissues were excised and fixed in Tissue-Tek (Sakura, Netherland) solution and cut into 4 μm sections in a cryostat. The sections were placed on slide glass for H & E (hematoxylin-eosin) staining and immunohistochemical staining. To eliminate peroxidase, the tissues were cultured in 3.0% $H_2O_2$, followed by washing with TBS buffer (0.05 M, pH 7.6). The slide was reacted in 5% skim milk solution at room temperature for 1 hour, followed by reaction with caveolin-1 antibody (BD transduction, 1:100) and myogenin antibody (Santa Cruz Biotechnology Inc., 1:100) at 4° C. for overnight. Avidin-biotin peroxidase complex staining was performed using LSAB kit (DAKO, Denmark), and counter staining was performed using hematoxylin. The slide was dehydrated with ethanol, washed with xylene and fixed with permount.

8. Extraction and Isolation of Caveolae

Caveolae was isolated in the absence of a surfactant according to the method of Song, et al (8). Briefly, virus-infected skeletal muscle cells (L6) were washed with ice-cold PBS and scraped using 1 ml of 0.5 M $NaCO_3$, pH 11.0 buffer, followed by homogenization. The homogenized cells were mixed with equal amount of 80% sucrose solution in MES buffer (25 mM MES, pH 6.5, 0.15 M NaCl), and the mixture was loaded in an ultracentrifuge tube. 4 ml of 30% sucrose (dissolved in MES) containing 0.25 M $Na_2CO_3$ and 4 ml of 5% sucrose (dissolved in MES) were added thereto. Centrifugation was performed at 39,000 rpm for 18 hours using Sw41 rotor (Beckman, Fullerton, Calif.). 12 fractions from the top of the gradient were collected and were divided with caveolin fractions which express the caveolin protein and non-caveolin fraction which don't express caveolin.

9. Construction and Analysis of Short Hairpin Lenti-Caveolin-1 Virus Vector

Short hairpin RNA lentivirus vector (shelenti-cav-1) targeting caveolin-1 gene was constructed by inserting two strands of oligonucleotides (5'-CGGAATTCCATCTA-CAAGCCCAACAACttcgGTTGTTGGGCTTGTAGAT-TTTTTATATCTAGACA-3') into EcoR I-Xba I restriction enzyme site of shLenti1.1-lentivirus vector (Macrogen, Seoul, Korea) (lower case, under-lined letters indicate loop of hair-pin loop without complementary sequence). The shLenti1.1-lentivirus vector was designed to produce shRNA from U6 promoter and then to express GFP protein from IRES system. As the control vector (shlenti-GFP), the oligonucleotide (5'-AATCGCATAGCGTATGCCGTT-3') was inserted into shLenti1.1 lentivirus vector. To investigate transfection efficiency on cells, L6 cells were infected with lentivirus vector ($3 \times 10^5$ MOI). GFP expression in the transfected cells was measured using fluorescent microscope and protein immunodetection.

Shlenti-caveolin-1 and shlenti-GFP vectors ($3 \times 10^7$ MOI) were injected intramuscularly into the hind limb of 30 week-old C57BL/6 mice. To investigate in vivo transfection efficiency, muscle tissues were cut into 4 μm sections, followed by immunohistochemical staining.

10. Construction and Analysis of Adenovirus Caveolin-1 Vector

Infectious recombinant adenovirus was made using the AdEasy method (20). Recombinant adenovirus expressing caveolin-1 (Ade-cav-1) was constructed by inserting the wild-type caveolin-1 cDNA into shuttle plasmid (pAdTRACK-CMV; Invitrogen). Homologous recombinant was performed in E. coli. BJ5183 with the shuttle plasmid. Recombinant virus was selected with kanamycin, and then was digested with restriction enzyme. Infectious adenovirus were produced following Transfection of the linearized recombinant adenovirus plasmid in HEK293 cells.

Infectious adenovirus were amplified in HEK293 cells on 15 cm plates, and purified using BD Adeno-X purification kit (Clontech, Palo Alto, Calif.). The control vector (Ade-GFP) was constructed by using the cDNA with green fluorescent protein. The efficiency of Ade-caveolin-1 and Ade-GFP was investigated by measuring GFP expression and by protein immunodetection.

30-week-old diabetic JYD were infected by intramuscular injection with Ade-GFP and Ade-cav-1 ($3 \times 10^{11}$ PFU/mouse. In vivo transfection efficiency was confirmed by immunohistochemical staining and in vivo fluorescence image using IVIS imaging system 100 series (Xenogen, Alameda, Calif.) (21).

11. Statistics

All experiment results was presented as mean±standard deviation. Statistic analyses was performed using 1-xay factorial ANOVA and pair-wise comparisons were evaluated by Fisher's least significant differences.

Statistical significance was assumed at $P<0.05$.

<Results>

1. Validity of JYD Mouse as Type II Diabetes Model

To investigate diabetes development in JYD mouse, blood glucose levels were compared between male JYD mouse and male C57BL/6 and DBA2 mice. The mean blood glucose level in 10-week-old male JYD (182.8 mg/dl) was significantly higher than that of the control male C57BL/6 (163.0 mg/dl) or DBA/2 (151/3 mg/dl). The blood glucose level in 30-week-old male JYD was even higher than that in the 10-week-old mouse (FIG. 1A). If blood glucose level was more than 250 mg/dl, it was diagnosed as diabetes (22). Diabetes incidence rate in 30-week-old male JYD (51%, 24/47) was significantly higher than that of male C57BL/6 or DBA/2 mice at the same ages (8.7%, 4/46 and 2.2%, 1/46, FIG. 1B). Diabetes incidence rate in female JYD was 10.6%, while diabetes was not developed in male C57BL/6 and DBA/2 mice at the same age (FIG. 1B) and male JYD (data not shown). Body weight of 10-week-old male JYD was significantly heavier than that of male C57BL/6 or DBA/2 at the same ages, but there was no significant difference in weights when they were both at 30 weeks (FIG. 1C). In the meantime, female JYD maintained normal blood glucose level and normal weight (data not shown).

2. Glucose and Insulin Resistance Test

Figure 2:
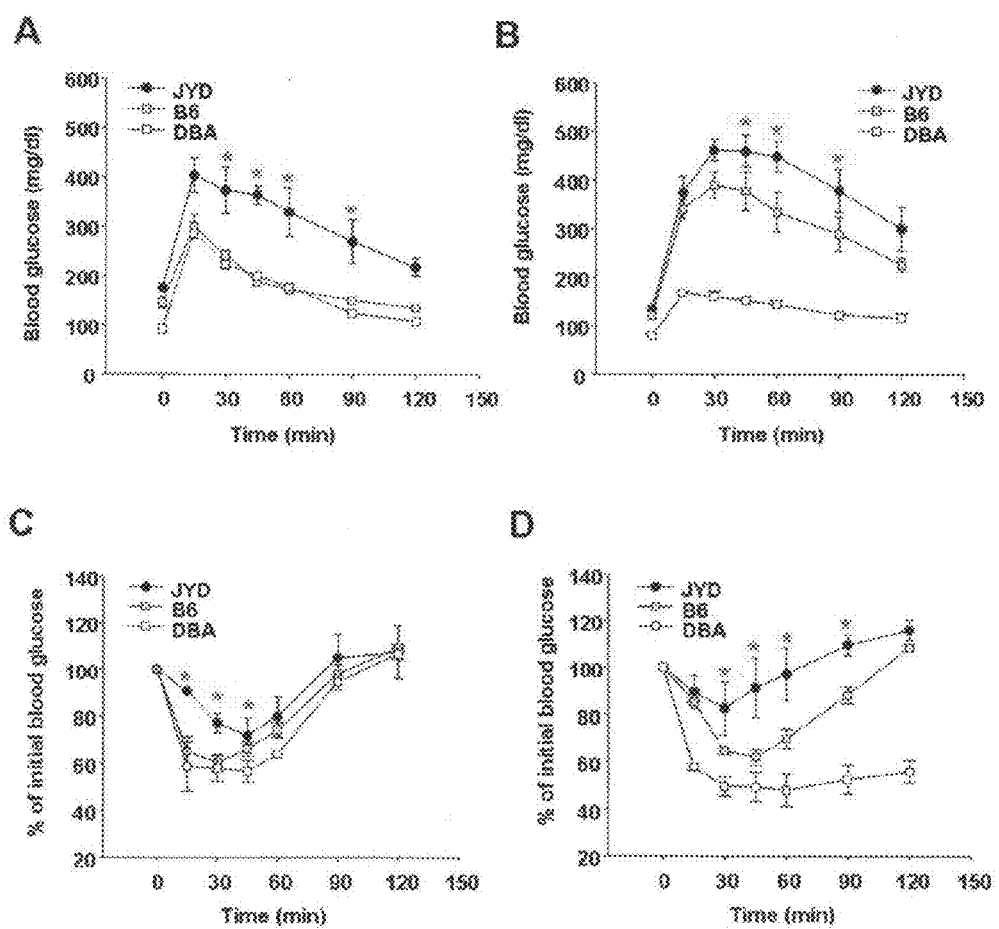
FIG. 2 is a set of graphs illustrating the glucose and insulin resistance of male JYD mouse. A and B: glucose resistance, C and D: insulin resistance. At this time, resistance of male JYD mouse was measured at 10 weeks (A, C) and at 30 weeks (B, D). Male C57BL/6 (B6) and DBA/2 (DBA) were used as the control. The value was presented as mean±standard deviation. n=6/group. *: P<0.05 (compared with JYD mouse), and **: P<0.01 (compared with JYD mouse).

Glucose resistance test was performed with male JYD mice at 10 and 30 weeks of age. Maximum blood glucose concentration in 10-week-old JYD was observed 15 minutes after glucose injection, and blood glucose level in JYD was significantly higher than that of male C57BL/6 and DBA2 all through the experiment (FIG. 2A). Glucose resistance of 30-week-old male JYD seemed to be more damaged than that of 10-week-old male JYD. Glucose resistance of male 57BL/6 at 30 weeks was also damaged. In the meantime, male DBA/2 could eliminate foreign glucose normally (FIG. 2B). Male JYD mouse was also tested for insulin resistance in order to investigate any problems with insulin sensitivity. Blood glucose concentration of 10-week-old male JYD was not significantly reduced, compared with that of C57BL/6 or DBA/2 after insulin injection (FIG. 2C). 10-week-old male JYD did not respond to foreign insulin, so that blood glucose level was not reduced (FIG. 2D).

3. Measurement of Glucose Metabolism Rate Using Positron Emission Tomography

Figure 3:
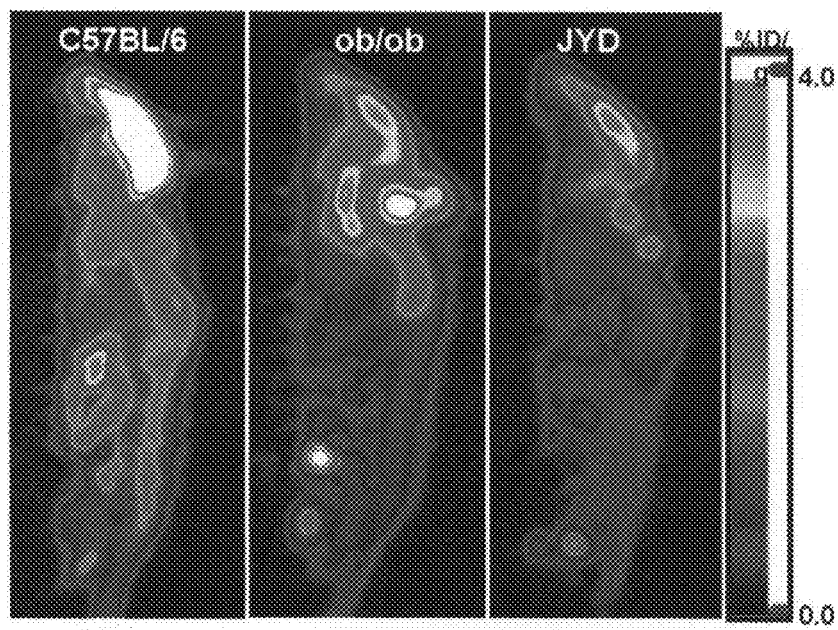
FIG. 3 illustrates the imaging results of positron emission tomography with male JYD mouse. Glucose absorption was measured using F-FDG PET. A: images crossing skull of each C57BL/6 (left), ob/ob (center) and JYD (right) mouse, and B: diagram showing each tissue and its corresponding region of a frozen mouse. Herein, % ID/g indicates the percentage of inserted amount per gram.
Figure 3:
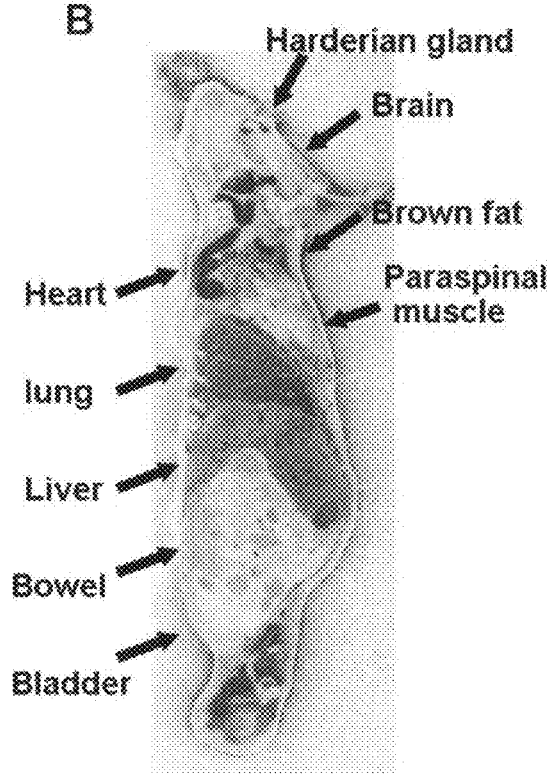

Type II diabetes patients exhibit reduced in vivo glucose utilization, so that radioactive fluoro-Deoxyglucose (FDG) absorption rate becomes low (23). Resional glucose metabolic rates has been measured by quantifying FDG in tissues using positron emission tomography (24). Based on that, the present inventors measured general glucose utilization in male JYD. C57BL/6 and ob/ob mice were used as the control. FDG absorption rate in 30-week-old C57BL/6 was particularly high in the brain, lung and spine, compared with that of JYD or ob/ob mouse at the same ages (FIG. 3). General glucose absorption rate in JYD was similar to that in ob/ob.

Figure 4:
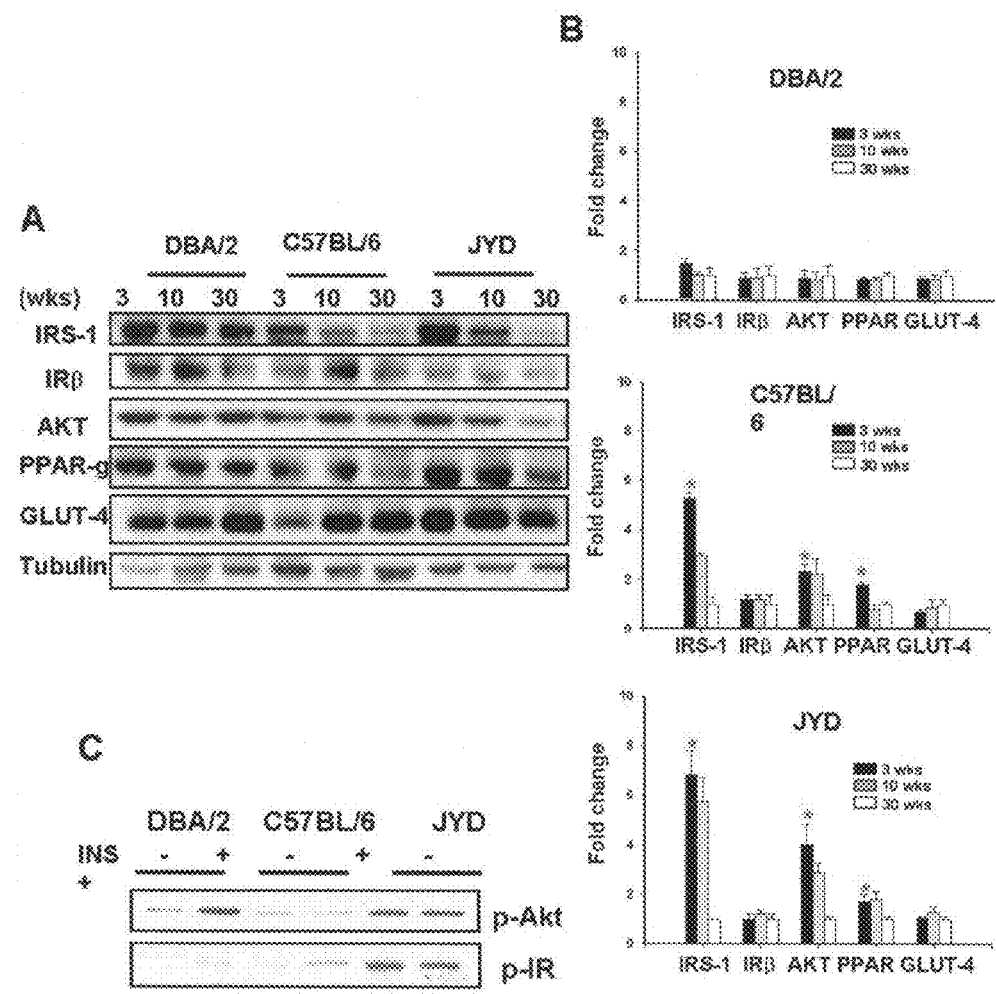
FIG. 4 illustrates the expression levels of phosphorylated proteins and insulin related proteins in JYD mouse muscle. A: expression levels of insulin related proteins isolated from male DBA/2, C57BL/6 and JYD mice at 3, 10 and 30 weeks, measured by protein immunodetection. Tubulin was used to prove that equal amounts of proteins were used. B: amounts of proteins measured by protein immunodetection. The amount of protein measured at the mouse at 30 weeks was used as the control. Proteins were increased at the mice at 3 weeks and the amounts of the proteins were calculated by densitometric analysis. Each bar graph indicates mean±standard deviation. *: P<0.05 (compared with the amount at 30 weeks). n=3/group. C: expression levels of phosphorylated Akt (p-Akt) and IR (p-IRβ) in skeletal muscles of insulin treated mice at 30 weeks (+) (INS) and insulin-not-treated mice at 30 weeks (−), measured by protein immunodetection.

4. Expressions of Insulin Signal Transduction Proteins and Phosphorylated Proteins in Skeletal Muscle Tissue To investigate age-dependent type II diabetes development mechanism in JYD mouse, expressions of insulin signal transduction proteins such as insulin receptor substrate (IRS-1), insulin receptor β (IRβ), Akt/PKB (Akt/protein kinase B), PPAR-β (peroxisome proliferators-activated receptor β), and glucose transporter-4 (GLUT-4) were measured in JYD at 3, 10 and 30 weeks age and the controls DBA/2 and C57BL/6 at the same ages (FIG. 4A). Expression levels of IRS-1, Akt/PKB and PPAR-β were significantly reduced age-dependently in JYD and C57BL/6. In the meantime, expression levels of IR β and GLUT-4 were not changed (FIG. 4B). Expression levels of the said proteins were not changed according to aging in DBA/2 (FIG. 4B).

Insulin function can be damaged not only by the changes of expressions of those proteins involved in insulin signal transduction but also by the changes of their activities (25). Therefore, the present inventors measured phosphorylation levels of IRβ and Akt/PKB after injecting insulin into DBA/2, C57BL/6 and JYD at 30 weeks age. Phosphorylation levels of IRβ and Akt/PKB were increased by the injection of insulin in DBA/2. However, phosphorylation levels of IRβ and Akt/PKB in C57BL/6 and JYD were not much changed, compared with that of the control (FIG. 4C). The above results indicate that insulin sensitivity of C57BL/6 or JYD at 30 weeks was damaged by down-regulations of those proteins involved in insulin signal transduction and decrease of those protein activities.

5. Expression of Caveolins in Skeletal Muscle Tissues and Insulin Related Tissues To investigate involvement of caveolins in diabetes development mechanism in JYD mouse, the present inventors measured caveolin expression levels in muscle tissues of DAB/2, C57BL/6, and JYD at 3, 10 and 30 weeks, and as a result it was confirmed that caveolin-1 expression was increased over the weeks by protein immunodetection (FIG. 5A). While caveolin-1 expression was increased 8 times in muscle tissues of DBA/2 or C57BL/6, the expression was increased about 2 times in muscle tissues of JYD (FIG. 5B). In the meantime, skeletal muscle tissue specific caveolin-3 expression was not changed over the weeks in DBA/2, JYD and C57BL/6.

Caveolin-1 expression levels in adipose tissues, livers and pancreases of DAB/2, C57BL/6, and JYD at 3, 10 and 30 weeks age were also investigated. As shown in FIG. 5A, the increase of caveolin-1 expression levels over the age in those tissues was significantly low in JYD, compared with in C57BL/6 and DBA/2, and changes in other tissues were not as significant as in skeletal muscles.

There is a report that aged muscle tissues can contain adipose tissues (26). To exclude the chance that caveolin-1 expressed in muscle tissues was originated from adipose cells in the aged skeletal muscle tissues, the present inventors measured the adipogenin gene leptin and the skeletal muscle tissue marker myogenin in skeletal muscle tissues of the mouse at 30 weeks by RT-PCR. As shown in FIG. 5C, leptin expression was detected specifically in adipose tissues, while myogenin was detected specifically in skeletal muscles tissues. Therefore, it was confirmed that caveolin-1 expressed in skeletal muscle tissues was not originated from adipose tissues. It was also confirmed by immunohistochemical staining that caveolin-1 expression level in skeletal muscle tissues of JYD at 30 weeks age was lower than that of C57BL/6 or DBA2 mouse (FIG. 5D), which was consistent with the result of protein immunodetection (FIGS. 5A and 5B).

The present inventors also investigated caveolin-1 expression levels in F1 male and female mice without diabetes. As shown in FIG. 5E, caveolin-1 expression level in the non-diabetic mice was higher than that in the diabetic mice.

Figure 5:
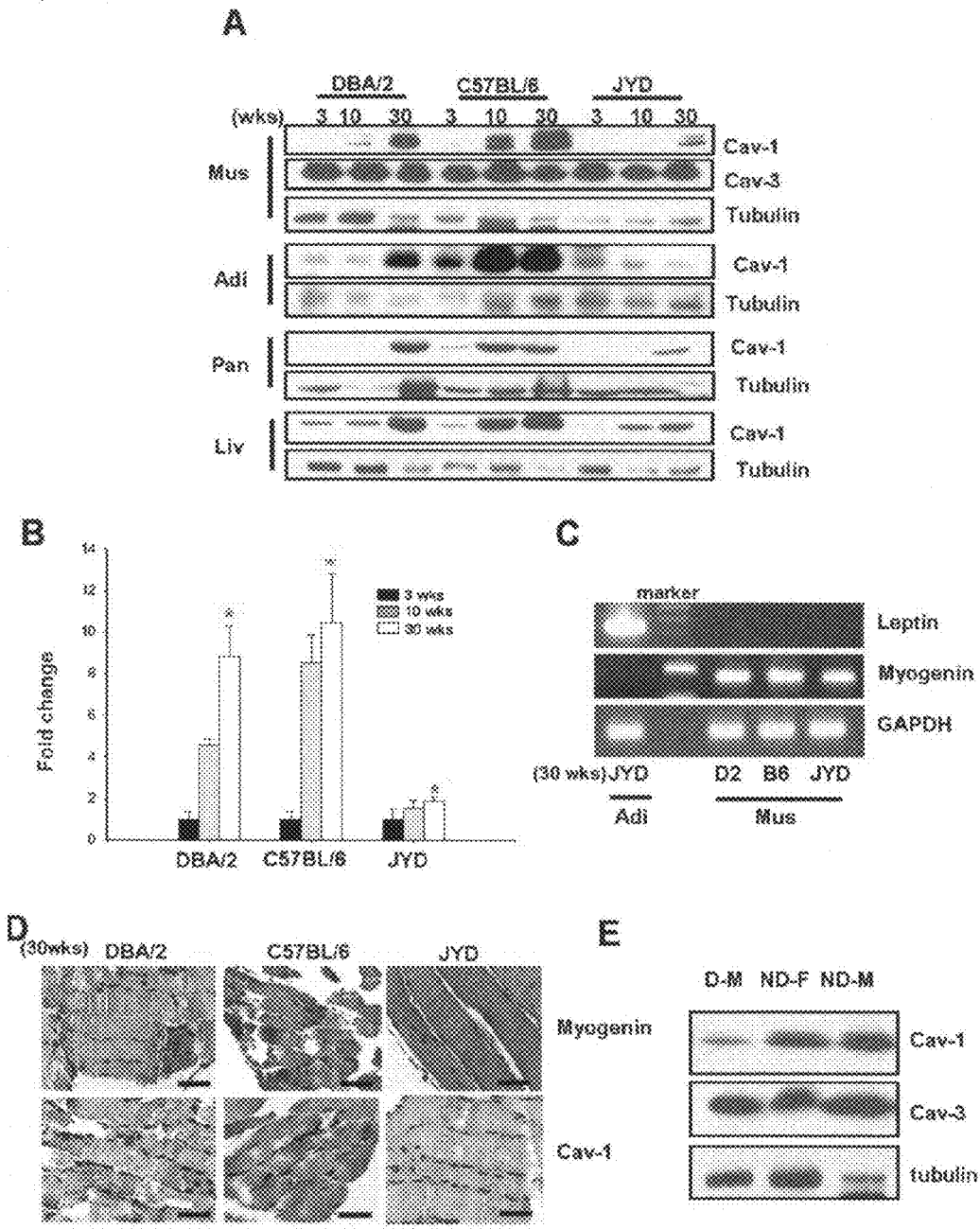
FIG. 5 illustrates the caveolin expression levels in muscle tissues and other insulin sensitive tissues. Tissues were isolated from mice, followed by protein immunodetection to measure the caveolin expression. A: expression levels of caveolin-1 (Cav-1) and caveolin-3 (Cav-3) in skeletal muscles (Mus), adipose tissues (Adi), pancreas (Pan) and livers (Liv) isolated from DBA/2, C57BL/6 and JYD mice at 3, 10 and 30 weeks, measured by protein immunodetection. Tubulin was used to prove that equal amounts of proteins were used. B: amounts of proteins in JYD mouse skeletal muscles measured by protein immunodetection. The amount measured at 3 weeks was used as the control and expression level at 30 weeks was measured by densitometric analysis. Each graph indicates mean±standard deviation. *: P<0.05 (compared with the amount at 3 weeks). n=3/group. C: mRNA levels of leptin and myogenin in skeletal muscles (Mus) and adipose tissues (Adi) of DBA/2 (D2), C57BL/6 (B6) and JYD (JYD) mice at 30 weeks, measured by RT-PCR. GAPDH mRNA was used to prove that equal amount of RNA was used. D: myogenin and caveolin-1 in muscle tissues of DBA/2, C57BL/6 and JYD mice at 30 weeks, measured by immunohistochemical staining (bar=100 μm). E: expression levels of caveolin in muscle tissues of the first generation JYD mouse having diabetes and the first generation JYD mouse not-having diabetes. D-M: male mouse with diabetes, ND-F: female mouse without diabetes, and ND-M: male mouse without diabetes.
Figure 6:
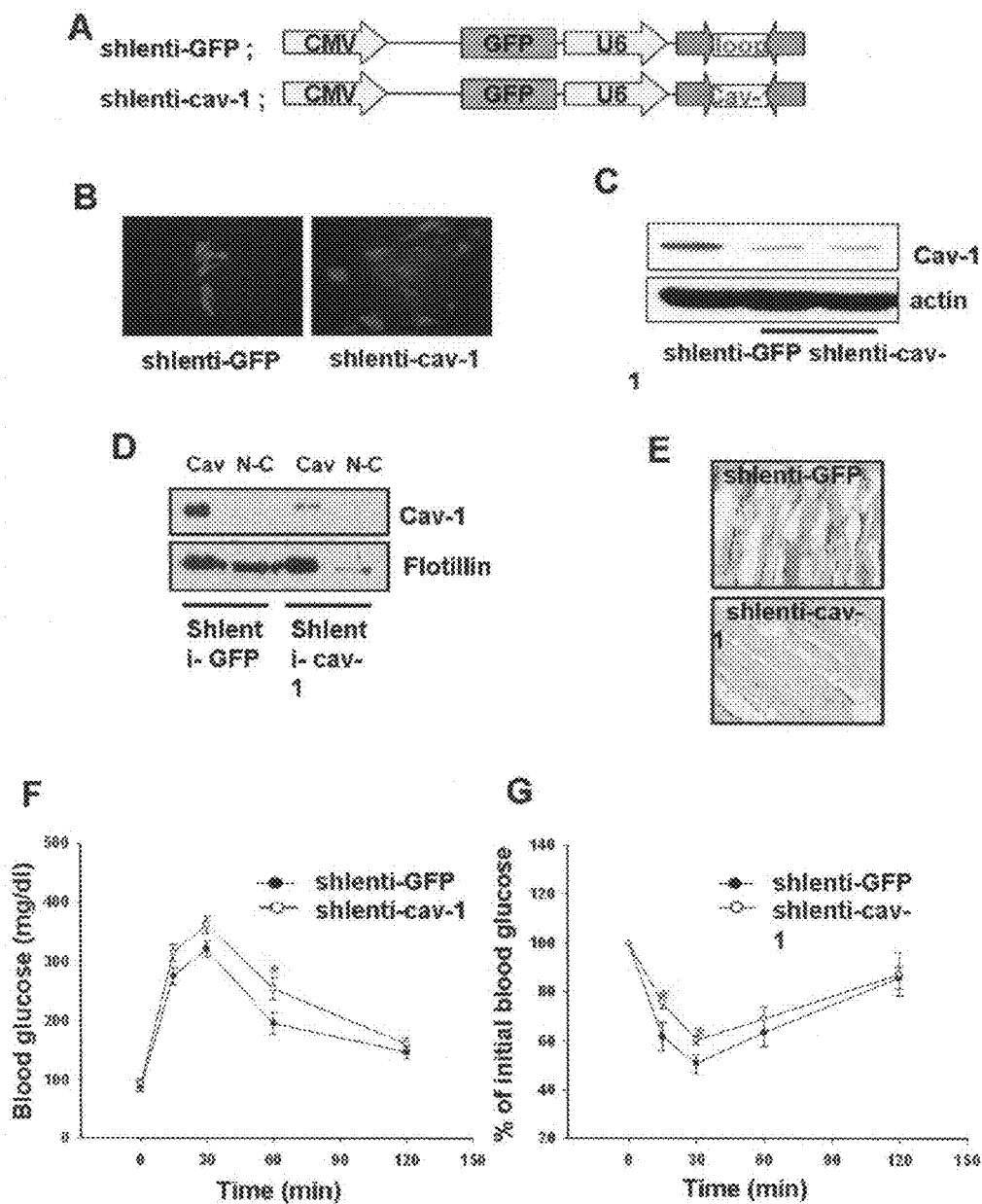
FIG. 6 illustrates the changes of glucose resistance or insulin resistance in C57BL/6 mice treated with shlenti-caveolin-1. A: diagram illustrating the lentivirus gene expression vehicle expressing caveolin-1 cDNA (shlenti-cav-1) and the control virus (shlenti-GFP). B: L6 cells infected with lentivirus observed under fluorescent microscope. C: caveolin-1 protein expression levels in L6 cells transfected with virus, measured by protein immunodetection. Actin was used to prove that equal amounts of proteins were used. D: expression levels of caveolin- and flotillin. Muscle cells infected with shlenti-GFP and shlenti-cav-1 were homogenized in the absence of a detergent, followed by pulverization, and then sucrose density gradient fraction was performed (caveolae fraction (cav), non-caveolae fraction (N-C)). Caveolin-1 expression was observed by protein immunodetection, and flotilin expression was used as a marker for lipid raft of cell membrane. E: caveolin-1 expression levels in leg skeletal muscles of C57BL/6 at 30 weeks injected with shlenti-cav-1 and shlenti-GFP ($3\times10^7$ MOI), measured by immunohistochemical staining. F: graph showing the result of glucose resistance test. G: graph showing the result of insulin resistance test. Each resistance test was performed 2 weeks after the injection of shlenti-GFP and shlenti-cav-1 virus. The marked time indicates lapse (min.) from the injection of glucose (F) or insulin (G) and the values are presented by mean±standard deviation. *: P<0.05 (compared with shlenti-GFP). n=5/group.

6. Caveolin-1 Down Regulation with Lentivirus Decrease Glucose Resistance and Insulin Sensitivity in C57BL/6 Mouse There is reported that caveolin-1 but not caveolin-3 is significantly up-regulated in aging in JYD mouse over the age, compared with in C57BL/6 and DBA mice, and caveolin-1 involved in adipose cells plays an important role in glucose metabolism and energy homeostasis (10). The present inventors focused on the effects of caveolin-1 on insulin sensitivity in skeletal muscles of JYD mouse, the diabetic animal model with non-obesity. Caveolin-1 expression was significantly increased in C57BL/6 and DBA/2, compared with in JYD (FIG. 5). So, the present inventors wondered if down-regulation of caveolin-1 had negative effect on glucose and insulin resistance in C57BL/6 mice. To answer this question, the inventors constructed lentivirus expressing short hairpin RNA that is known to reduce caveolin-1 expression which was designed to express GFP as a marker. GFP-expressing lentivirus containing scrambled nucleotide sequence was used as the control (FIG. 6A). First, the efficiency of lentivirus-mediated caveolin-1 down-regulation at L6 cell level was investigated on L6 cells. It was confirmed with fluorescent microscope that L6 cells were successfully infected with the virus (FIG. 6B) and it was also confirmed by protein immunodetection that shlenti-caveolin-1 infection caused decrease of caveolin expression (FIG. 6C). After sucrose density gradient fractionation, caveolae fraction/non-caveolae fraction was investigated. As a result, caveolin-1 expression in caveolae fraction was reduced in the cells infected with shlenti-caveolin-1 (FIG. 6D). The present inventors intramuscularly injected shlenti-GFP or shlenti-caveolin-1 into 30 week-old C57BL/7 mice. As shown in FIG. 6E, it was confirmed by immunohistochemical method that caveolin-1 expression was reduced in skeletal muscles treated with shlenti-cav-1, compared with in skeletal muscles treated with shlenti-GFP. At 2 weeks after the injection, shlenti-virus expression efficiency was reduced (data not shown), so experiments were performed in two weeks with the viral injection. At 12 days after the virus injection, blood glucose level of the mouse injected with shlenti-caveolin-1 was significantly reduced, compared with that of the control (data not shown). At 14 days after the virus injection, the caveolin-1 down-regulated mice showed more severe impairment of glucose and insulin resistance, compared with in the mouse injected with shlenti-GFP (FIGS. 6F and 6G). As a result, weights were not much changed even after 4 weeks from the lentivirus injection (data not shown).

7. Caveolin-1 Up-regulated with Adenovirus Increase Glucose Resistance, Insulin Resistance and Glucose Absorption in 30 Week-old JYD Mouse.

Figure 7:
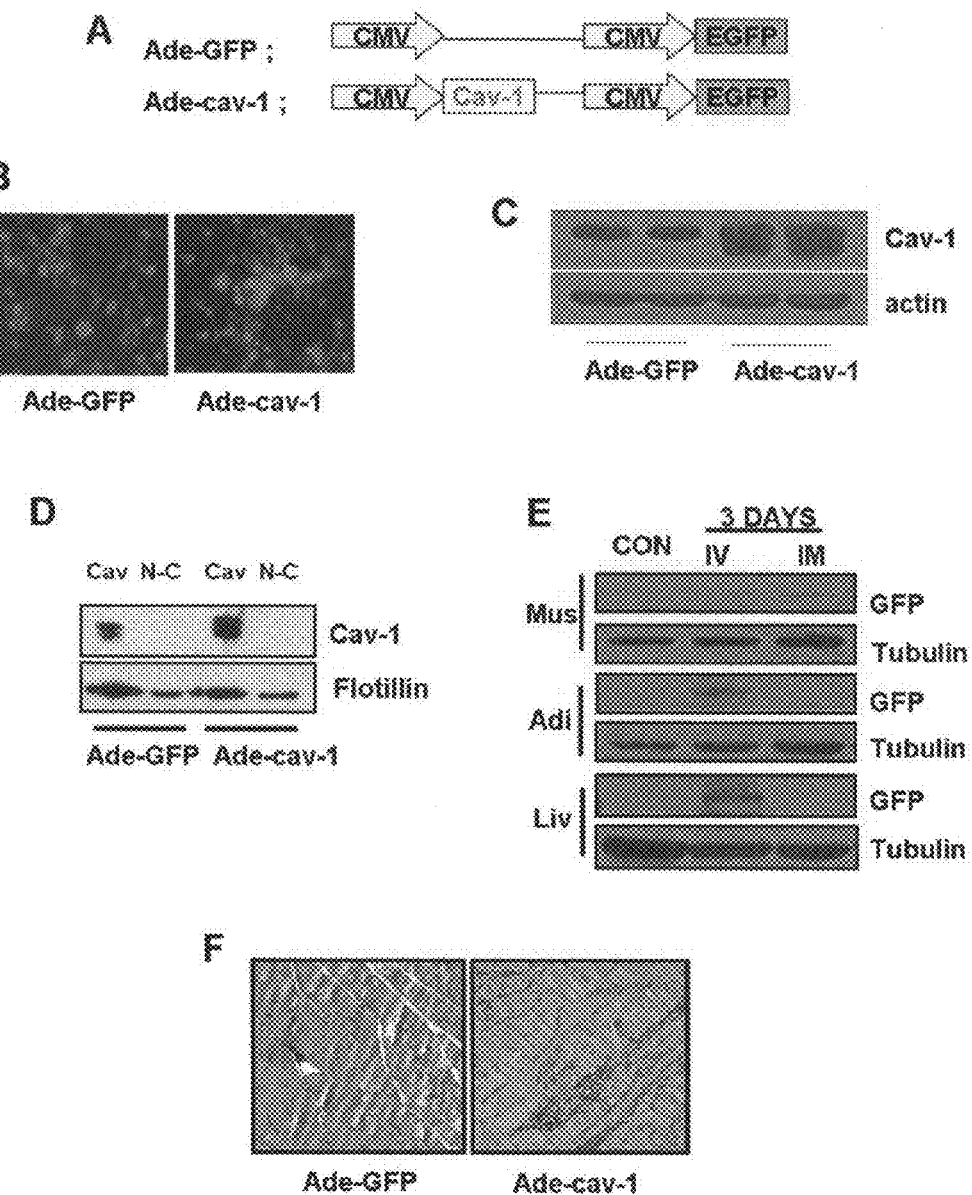
FIG. 7 illustrates the results of construction and analysis of adenovirus caveolin-1 vehicle. A: diagram illustrating the adenovirus gene expressing mouse caveolin-1 cDNA (Ade-cav-1) and the control vehicle (Ade-GFP). B: infected L6 cells observed under fluorescent microscope. C: caveolin-1 protein expression levels in transfected L6 cells, measured by protein immunodetection. Actin expression was regarded as the control. D: expression levels of caveolin-1 and flotillin. Muscle cells infected with Ade-GFP and Ade-cav-1 were homogenized in the absence of a detergent, followed by pulverization, and then sucrose density gradient fraction (fraction 1-12) was performed (caveolae fraction (cav), non-caveolae fraction (N-C)). Caveolin-1 expression was observed by protein immunodetection, and flotillin expression was used as a marker for lipid raft of cell membrane. E: expression levels of GFP. Ade-GFP was injected into muscle of a mouse. The mouse was sacrificed three days after the injection and GFP protein levels in muscle (Mus), adipose tissue (Adi), and liver (Liv) of the mouse were investigated by protein immunodetection. Ade-GFP was injected into tail vein (IV), which was used as the control. Tubulin expression was regarded as the control. CON (control) indicates that saline was injected into muscle of the mouse. F: caveolin-1 expression levels in leg skeletal muscles of JYD at 30 weeks injected with Ade-cav-1, or Ade-GFP ($3\times10^{11}$ PFU), measured by immunohistochemical method.

Since caveolin-1 expression was significantly reduced in JYD mouse, compared with in C57BL/6 mouse, the present inventors had a question if over-expression of caveolin-1 could have positive effect on glucose and insulin resistance in 30 week-old JYD mouse. GFP expressed adenovirus vector was used as the control and adenovirus expressing caveolin-1 and GFP together was also used (FIG. 7A). First, efficiency of virus over-expressing caveolin-1 was measured in L6 cells. It was confirmed successful virus infection using the fluorescent microscope (FIG. 7B). It was also confirmed by protein immunodetection that caveolin-1 expression was increased in the cells infected with caveolin-1 adenovirus, compared with in the cells infected with the control virus (FIG. 7C). After sucrose density gradient fractionation, caveolae fraction/non-caveolae fraction was investigated. As a result, it was confirmed that caveolin-1 expression was increased in caveolae fraction of the cells infected with Ade-cav-1 (FIG. 7D). To investigate whether intramuscular injection of the adenoviral vector would affect other tissues, the present inventors examined injected Ade-GFP ($3 \times 10^{11}$ pfu) (adenovirus expressing GFP only) into intramuscular and examined skeletal muscles, adipose cells and liver. Protein immunodetection (FIG. 7E) and fluorescence imaging (data not shown) was. shown that the GPF was observed in skeletal muscles only. That of intravenous injected GPF was shown fluorescence in other tissues. When Ade-cav-1 (adenovirus containing caveolin-1) was injected into the skeletal muscle of JYD mice. immuno-staining results was shown caveolin-1 expression was increased as compared with Ade-GFP-injected mice (control) (FIG. 7F). It was confirmed by in vivo fluorescence imaging that caveolin-1 expression reached maximum level three days after the injection (data not shown). Therefore, the experiments was performed at three days after the virus injection.

Figure 8:
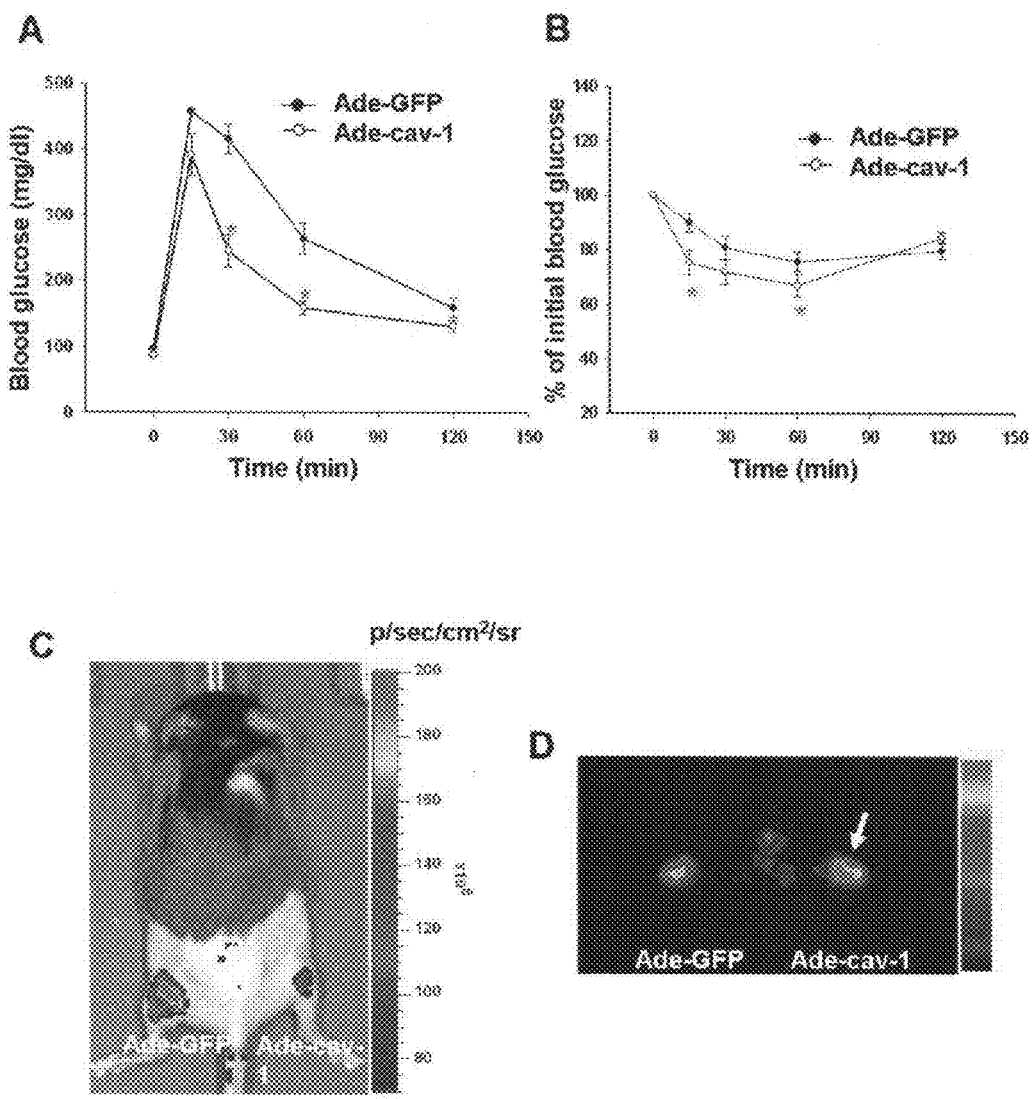
FIG. 8 illustrates the glucose and insulin resistance promotion by the injection of Ade-caveolin-1 into JYD mice. Three days after the injection of adenovirus, the mice were fasted for 18 days, followed by glucose resistance test (A) and insulin sensitivity test (B). Time (minutes) indicates lapse from the injection of glucose or insulin. The results are presented as mean±standard deviation. *: P<0.05 (compared with Ade-GFP). n=6/group. C: photograph illustrating the efficiency of genetic phenotype change in the mouse injected with the control (Ade-GFP, left) or caveolin-1 (Ade-Cav-1, right). Fluorescence level is presented by p/sec/cm²/sr. D: glucose absorption measured by positron emission tomography using 18F. Red: high glucose absorption. Black: low glucose absorption. Image indicates cross-section of the JYD mouseinjected with Ade-GFP or Ade-cav-1.

At Three days after injecting Ade-cav-1 or Ade-GFP into skeletal muscles of JYD mice, glucose and insulin resistance test was performed. When Ade-cav-1was injected, foreign glucose was more effectively eliminated, compared with when the Ade-GFP (control) was injected (FIG. 8A). It was also confirmed that blood glucose level was significantly reduced by the injected foreign insulin in the mouse infected with Ade-cav-1, suggesting that insulin sensitivity was increased in the mouse (FIG. 8A). Ade-GFP and Ade-cav-1were injected respectively to each side of legs of JYD, followed by investigation of glucose absorption by positron emission tomography (23). Three days after the injection, it was confirmed that glucose absorption in the skeletal muscles injected with Ade-cav-1was increased, compared with that of the control (FIGS. 8C and 8D). These results indicate that over-expression of caveolin-1 promotes glucose absorption in skeletal musclesand thereby plays an important role in increasing insulin sensitivity of JYD mouse.

<Discussion>

The present inventors observed that as male JYD mice got old, moderate hyperlipiclema was developed into serious hyperlipidemia but the mice did not show obesity, compared with the parental C57BL/6 and DBA. So, it is believed that JYD mouse is a proper animal model for the study of age-dependent type II diabetes, one of adult disease.

Skeletal muscleis the basic tissue for insulin mediated glucose absorption. In the meantime, glucose absorption is very slow in adipose tissue and such glucose absorption in adipose tissue takes only 2-3% of the total glucose absorption (27). Many studies examing the role of againg on glucose absorption have demonstrated the decreased muscular insulin sensitivity (28, 29). These studies suggest that insulin resistance in skeletal muscle is very important in elderly people. However, precise mechanism of age-dependent glucose absorption in the skeletal muscle has not been disclosed, yet. So, the present inventors focused on that and continued to study with JYD mouse.

If there is insulin resistance in peripheral tissue, blood glucose cannot be effectively absorbed or metabolized in tissues, leading to hyperlipidemia. Male JYD mice could not effectively eliminate exogenous glucose, compared with the parental DBA/2 mice, and exogenous insulin could not lower blood glucose level, either. Glucose resistance of C57BL/6 mice was confirmed to be impaired at 30 weeks of age, and insulin response was also abnormal. However, C57BL/6 mice did not develop into serious hyperlipidemia, compared with male JYD mice.

Insulin stimulates insulin receptor, which activate phosphorylation of PI3-kinase (phosphatidylinositol 3-kinase), Akt/PKB and phosphorylated residue of insulin receptor (30, 31). Such activation of the signal transduction system promotes glucose transport through glucose receptor-4 and glucose metabolism. IRS is the link between insulin receptor and other signal transduction molecules such as PI3-kinase (31). Therefore, decreased expression of such molecules involved in signal transduction pathway or their malfunction results in insulin resistance (32). For example, any defect in the insulin-signal transduction pathway, such as inhibition of expression of insulin receptor IRS-2 (33), or Akt (34), can cause type II diabetes.

To elucidate the mechanism of age-dependent type II diabetes, the present inventors analysed insulin signal transduction proteins in skeletal muscle tissues. The inventors observed impaired glucose and insulin resistance in C57BL/6 and JYD mice at 30 weeks of age, which was presumably attributed to the decrease of IRS-1, Akt/PKB, or PPAR-$\beta$ expression and the decrease of phosphorylation of IR$\beta$ and Akt/PKB by insulin injection. However, diabetes incidence rate in C57BL/6 (8.7%) was significantly lower than that in JYD (51%). This result indicates that diabetes is caused by another defect in addition to defect of direct insulin signal transduction system.

In the previous study, the present inventors reported that caveolin is an important cell membrane molecule, which plays an important role in cellular aging (35). So, the present inventors further investigated age-dependent caveolin expression level in parental mice and JYD mice. As a result, caveolin-3 expression level was not changed with age in every mouse. Interestingly, caveolin-1 expression level was increased with age in skeletal muscle tissues of every mouse over the weeks. However, the increasing rate of the expression level was higher in C57BL/6 and DBA/2 mice than in JYD. The above results indicate that a detect in caveolin-1 plays an important role in type II diabetes development and in insulin sensitivity in JYD mouse model. Consistent with this, insulin resistance was confirmed in the mouse in which caveolin-1 expression was reduced. In particular, the expressions of insulin receptor proteins were reduced in adipose tissues (10). Age-dependent caveolin expression was similar in other tissues to that in skeletal muscle tissues. But, the present inventors focused on insulin resistance in skeletal muscle tissues to study type II diabetes. Particularly, the inventors reported in the previous study that caveolin-1 plays an important role in glucose absorption in skeletal muscle cells (18), so that the inventors focused our further study on regulation of caveolin-1 level in skeletal muscle.

To investigate what kind of role caveolin-1 plays in regulation of insulin sensitivity, the present inventors reduced caveolin-1 expression in C57BL/6 micebut increased caveolin expression in JYD mice. When caveolin-1 was down-regulated by RNA interference in C57BL/6 mouse, blood glucose level was increased. In the meantime, glucose and insulin resistance was damaged, compared with that of the control C57BL/6. When caveolin-1 was over-expressed in JYD mice, glucose and insulin sensitivity was increased and glucose absorption in skeletal muscle was also increased. The present inventors also tested F1 generation without diabetes, generated by mating C57BL/6 and DBA. As a result, caveolin-1 expression level was higher than that in the mice having diabetes. The above results indicate that caveolin-1 level in skeletal muscle tissues is closely related to diabetes development in JYD mice.

Intracellular glucose transportation and usability seem to be the pathogenesis of insulin resistance (18, 32, 36). The present inventors confirmed previously that glucose receptor-4 is expressed only in cell membrane region containing caveolin (18, 37) and caveolin-1 is rather closely related to insulin dependent glucose absorption by glucose receptor-4 transportation in skeletal muscle cells than involved in changes of glucose receptor-4 expression level (18). Caveolin-1 is involved in cell migration and caveolae includes many molecules necessary for formation of receptor required for glucose transportation (31) including soluble N-ethylmaleimide-sensitive factor attachment receptor (SNARE) protein (38, 39). So, it is believed that caveolin-1 regulates such molecules to affect glucose receptor-4 migration. Over-expression of caveolin-1 in skeletal muscles induced by exercise can be also an important factor for insulin sensitivity (40). The above results indicate that up-regulation of caveolin-1 increases insulin sensitivity via glucose absorption system.

The present inventors compared age-dependent type II diabetes model JYD mouse and ob/ob mouse. To do so, the inventors measured expressions of not only caveolin but also insulin signal transduction related molecules in ob/ob mice. Interestingly, insulin resistance of ob/ob mouse showing obesity was confirmed to be caused by decrease of glucose receptor-4 in adipose cells (data not shown), and at the same time the inventors observed that caveolin-1 expression was not much different from that of the control mouse.

It was already reported that the caveolin-1 deficient mice exhibited insulin resistance in adipose tissues (10). However, this phenomenon is not age-dependent but is caused by the defective insulin receptor expression upon the caveolin-1 deficiency because the caveolin-1 directly interacted with insulin receptor in adipose tissues. In skeletal muscle, it was also reported that the caveolin-3 null mice showed insulin resistance by defective phosphorylation of IRβ and IRS-1/2 upon insulin injection. However, as reported in our previous reports, GLUT-4 transportation in skeletal muscle cells is carried out by different mechanism from IRβ signal transduction system known in adipose cells. So, caveolin-1 plays a different role in skeletal muscle from that in adipose tissues. In addition, caveolin-3 null mice exhibited abnormal skeletal muscle fiber formation in skeletal muscle (41). Caveolin-3 defect results in apoptosis of skeletal muscle cells by limb girdle muscular dystrophy and muscle disease (42). In caveolin-3 null mice, it is not clear whether insulin resistance is caused by caveolin-3 deficiency or defect of muscle tissue itself.

The previous studies on the mechanism of age-dependent type II diabetes have been carried on depended on animal models showing obesity (43-45). In this invention, it was confirmed that onset of type II diabetes was increased by aging and JYD model was appropriate for the study of age-dependent type II diabetes but not having obesity. In addition, the proof was provided that caveolin-1 status in JYD mouse skeletal muscle is an important factor involved in the mechanism leading to increased incidence of type II diabetes in old age not having obesity symptom.

In conclusion, the present inventors confirmed that down-regulation of caveolin-1 in skeletal muscle tissues of JYD mice, the type II diabetes model mice which is age-dependent and does not show obesity symptom, develops diabetes and at the same time the caveolin-1 expression can regulate insulin sensitivity of JYD mouse. Therefore, the method of the present invention is very effective in the improvement and treatment of diabetes by regulating insulin sensitivity by increasing caveolin level in skeletal muscle tissues of type II diabetes patient which is age-dependent but does not showing obesity symptom.

Reference

1. Saltiel A R 2001 New perspectives into the molecular pathogenesis and treatment of type 2 diabetes. Cell 104:517-29

2. Scheen A J 2005 Diabetes mellitus in the elderly: insulin resistance and/or impaired insulin secretion? Diabetes Metab 31 Spec No 2:5 S27-5S34

3. Kim D J, Song K E, Park J W, Cho H K, Lee K W, Huh K B 2007 Clinical characteristics of Korean type 2 diabetic patients in 2005. Diabetes Res Clin Pract 77 Suppl 1:S252-7

4. Park S Y, Choi G H, Choi H I, Ryu J, Jung C Y, Lee W 2005 Calorie restriction improves whole-body glucose disposal and insulin resistance in association with the increased adipocyte-specific GLUT4 expression in Otsuka Long-Evans Tokushima fatty rats. Arch Biochem Biophys 436:276-84

5. Kanemoto N, Hishigaki H, Miyakita A, et al. 1998 Genetic dissection of "OLETF", a rat model for non-insulin-dependent diabetes mellitus. Mamm Genome 9:419-25

6. Sargiacomo M, Scherer P E, Tang Z, et al. 1995 Oligomeric structure of caveolin: implications for caveolae membrane organization. Proc Natl Acad Sci USA 92:9407-11

7. Schlegel A, Lisanti M P 2000 A molecular dissection of caveolin-1 membrane attachment and oligomerization. Two separate regions of the caveolin-1 C-terminal domain mediate membrane binding and oligomer/oligomer interactions in vivo. J Biol Chem 275:21605-17

8. Song K S, Scherer P E, Tang Z, et al. 1996 Expression of caveolin-3 in skeletal, cardiac, and smooth muscle cells. Caveolin-3 is a component of the sarcolemma and co-fractionates with dystrophin and dystrophin-associated glycoproteins. J Biol Chem 271:15160-5

9. Cohen A W, Combs T P, Scherer P E, Lisanti M P 2003 Role of caveolin and caveolae in insulin signaling and diabetes. Am J Physiol Endocrinol Metab 285:E1151-60

10. Cohen A W, Razani B, Wang X B, et al. 2003 Caveolin-1-deficient mice show insulin resistance and defective insulin receptor protein expression in adipose tissue. Am J Physiol Cell Physiol 285:C222-35

11. Cho K A, Ryu S J, Park J S, et al. 2003 Senescent phenotype can be reversed by reduction of caveolin status. J Biol Chem 278:27789-95

12. Cho K A, Ryu S J, Oh Y S, et al 2004 Morphological adjustment of senescent cells by modulating caveolin-1 status. J Biol Chem 279:42270-8

13. Park W Y, Park J S, Cho K A, et al. 2000 Up-regulation of caveolin attenuates epidermal growth factor signaling in senescent cells. J Biol Chem 275:20847-52

14. Kawabe J I, Grant B S, Yamamoto M, Schwencke C, Okumura S, Ishikawa Y 2001 Changes in caveolin subtype protein expression in aging rat organs. Mol Cell Endocrinol 176:91-5

15. Li W P, Liu P, Pilcher B K, Anderson R G 2001 Cell-specific targeting of caveolin-1 to caveolae, secretory vesicles, cytoplasm or mitochondria. J Cell Sci 114:1397-408

16. Galbiati F, Volonte D, Engelman J A, Scherer P E, Lisanti M P 1999 Targeted down-regulation of caveolin-3 is sufficient to inhibit myotube formation in differentiating C2C12 myoblasts. Transient activation of p38 mitogen-activated protein kinase is required for induction of caveolin-3 expression and subsequent myotube formation. J Biol Chem 274:30315-21

17. Capozza F, Cohen A W, Cheung M W, et al. 2005 Muscle-specific interaction of caveolin isoforms: differential complex formation between caveolins in fibroblastic vs. muscle cells. Am J Physiol Cell Physiol 288:C677-91

18. Oh Y S, Cho K A, Ryu S J, et al. 2006 Regulation of insulin response in skeletal muscle cell by caveolin status. J Cell Biochem 99:747-58

19. Kafri T, Blomer U, Peterson D A, Gage F H, Verma I M 1997 Sustained expression of genes delivered directly into liver and muscle by lentiviral vectors. Nat Genet. 17:314-7

20. He T C, Zhou S, da Costa L T, Yu J, Kinzler K W, Vogelstein B 1998 A simplified system for generating recombinant adenoviruses. Proc Natl Acad Sci USA 95:2509-14

21. Park S W, Goodpaster B H, Strotmeyer E S, et al. 2007 Accelerated loss of skeletal muscle strength in older adults with type 2 diabetes: the health, aging, and body composition study. Diabetes Care 30:1507-12

22. Khil L Y, Jun H S, Kwon H, et al. 2007 Human chorionic gonadotropin is an immune modulator and can prevent autoimmune diabetes in NOD mice. Diabetologia 23. Voipio-Pulkki L M, Nuutila P, Knuuti M J, et al. 1993 Heart and skeletal muscle glucose disposal in type 2 diabetic patients as determined by positron emission tomography. J Nucl Med 34:2064-7

24. Phelps M E, Huang S C, Hoffman E J, Selin C, Sokoloff L, Kuhl D E 1979 Tomographic measurement of local cerebral glucose metabolic rate in humans with (F-18)2-fluoro-2-deoxy-D-glucose: validation of method. Ann Neurol 6:371-88

25. Bruning J C, Michael M D, Winnay J N, et al. 1998 A muscle-specific insulin receptor knockout exhibits features of the metabolic syndrome of NIDDM without altering glucose resistance. Mol Cell 2:559-69

26. Taylor-Jones J M, McGehee R E, Rando T A, Lecka-Czernik B, Lipschitz D A, Peterson C A 2002 Activation of an adipogenic program in adult myoblasts with age. Mech Ageing Dev 123:649-61

27. Baron A D, Laakso M, Brechtel G, Edelman S V 1991 Reduced capacity and affinity of skeletal muscle for insulin-mediated glucose uptake in noninsulin-dependent diabetic subjects. Effects of insulin therapy. J Clin Invest 87:1186-94

28. Broughton D L, Taylor R 1991 Review: deterioration of glucose resistance with age: the role of insulin resistance. Age Ageing 20:221-5

29. Ryan A S 2000 Insulin resistance with aging: effects of diet and exercise. Sports Med 30:327-46

30. Kanzaki M, Pessin J E 2003 Insulin signaling: GLUT4 vesicles exit via the exocyst. Curr Biol 13:R574-6

31. Saltiel A R, Kahn C R 2001 Insulin signalling and the regulation of glucose and lipid metabolism. Nature 414:799-806

32. Nandi A, Kitamura Y, Kahn C R, Accili D 2004 Mouse models of insulin resistance. Physiol Rev 84:623-47

33. Withers D J, Gutierrez J S, Towery H, et al. 1998 Disruption of IRS-2 causes type 2 diabetes in mice. Nature 391:900-4

34. Cho H, Mu J, Kim J K, et al. 2001 Insulin resistance and a diabetes mellitus-like syndrome in mice lacking the protein kinase Akt2 (PKB beta). Science 292:1728-31

35. Cho K A, Park S C 2005 Caveolin-1 as a prime modulator of aging: a new modality for phenotypic restoration? Mech Ageing Dev 126:105-10

36. Shulman G I 2000 Cellular mechanisms of insulin resistance. J Clin Invest 106:171-6

37. Barros R P, Machado U F, Warner M, Gustafsson J A 2006 Muscle GLUT4 regulation by estrogen receptors ERbeta and ERalpha. Proc Natl Acad Sci USA 103:1605-8

38. Schnitzer J E, Liu J, Oh P 1995 Endothelial caveolae have the molecular transport machinery for vesicle budding, docking, and fusion including VAMP, NSF, SNAP, annexins, and GTPases. J Biol Chem 270:14399-404

39. Liu P, Rudick M, Anderson RG 2002 Multiple functions of caveolin-1. J. Biol Chem 277:41295-8

40. Oh Y S, Kim H J, Ryu S J, et al. 2007 Exercise type and muscle fiber specific induction of caveolin-1 expression for insulin sensitivity of skeletal muscle. Exp Mol Med 39:395-401

41. Galbiati F, Engelman J A, Volonte D, et al. 2001 Caveolin-3 null mice show a loss of caveolae, changes in the microdomain distribution of the dystrophin-glycoprotein complex, and t-tubule abnormalities. J Biol Chem 276:21425-33

42. Smythe G M, Eby J C, Disatnik M H, Rando T A 2003 A caveolin-3 mutant that causes limb girdle muscular dystrophy type 1C disrupts Src localization and activity and induces apoptosis in skeletal myotubes. J Cell Sci 116:4739-<

43. Maedler K, Schumann D M, Schulthess F, et al. 2006 Aging correlates with decreased beta-cell proliferative capacity and enhanced sensitivity to apoptosis: a potential role for Fas and pancreatic duodenal homeobox-1. Diabetes 55:2455-62

44. Reznick R M, Zong H, Li J, et al. 2007 Aging-associated reductions in AMP-activated protein kinase activity and mitochondrial biogenesis. Cell Metab 5:151-6

45. Wheatcroft S B, Kearney M T, Shah A M, et al. 2007 IGF-bindingprotein-2 protects against the development of obesity and insulin resistance. Diabetes 56:285-94

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

The invention claimed is:

1. A method for improving type II diabetes of a mammal, comprising the step of administering a therapeutically effective amount of a pharmaceutical composition comprising recombinant adenovirus expressing caveolin-1 to skeletal muscle tissue of the mammal, wherein overexpression of caveolin-1 promotes glucose absorption in skeletal muscle, and wherein the type II diabetes is age-dependent but not showing obesity symptom.

2. The method according to claim 1, wherein the mammal is human.

* * * * *